(12) United States Patent
Rice

(10) Patent No.: US 6,395,950 B1
(45) Date of Patent: *May 28, 2002

(54) ISOMERIZATION WITH ADSORPTIVE SEPARATION AND DIVIDING WALL FRACTIONAL DISTILLATION

(75) Inventor: Lynn H. Rice, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/710,721

(22) Filed: Nov. 10, 2000

(51) Int. Cl.$^7$ .............................. C07C 5/13; C07C 7/12
(52) U.S. Cl. ...................... 585/738; 585/734; 585/737; 585/820; 585/825; 585/826
(58) Field of Search ................. 585/734, 737, 585/738, 820, 825, 826

(56) References Cited

U.S. PATENT DOCUMENTS

| | | | |
|---|---|---|---|
| 2,471,134 A | 5/1949 | Wright et al. | 196/100 |
| 3,201,491 A | 8/1965 | Stine et al. | 260/676 |
| 3,205,166 A | 9/1965 | Ludlow et al. | 208/310 |
| 3,510,423 A | 5/1970 | Neuzil et al. | 208/310 |
| 4,006,197 A | 2/1977 | Bieser | 260/676 |
| 4,036,745 A | 7/1977 | Broughton | 208/310 |
| 4,230,533 A | 10/1980 | Giroux | 203/1 |
| 5,177,299 A * | 1/1993 | McCullock et al. | 585/826 |

OTHER PUBLICATIONS

Gerd Kaibel; "Distillation Columns with Vertical Partitions"; Chem. Eng. Technol 10 (1987) 92–98.*
Rudd, H. "Thermal Coupling for Energy Efficiency" *Supplement to The Chemical Engineer* page s14–s15 Aug. 27, 1992.
Domergue, B and Watrepont L. "Advanced Recycle Paraffin Isomerization Technology" *World Refining* page 26–30 May 2000.

* cited by examiner

*Primary Examiner*—Thuan D. Dang
(74) *Attorney, Agent, or Firm*—John G. Tolomei; Frank S. Molinaro; Maryann Maas

(57) ABSTRACT

Construction and operational costs of recovering the high-octane components of an isomerization raffinate product of a simulated moving bed adsorptive separation process units are reduced by employing a dividing wall column to perform the separation. The raffinate product stream is passed into the column at an intermediate point on the first side of the dividing wall, with the column delivering the low-octane raffinate components as a sidedraw from the opposite side of the dividing wall. A stream of higher octane components are removed both as an overhead stream and a bottoms stream. The sidedraw may be recycled to the isomerization zone.

16 Claims, 3 Drawing Sheets

ISOMERIZATION WITH ADSORPTIVE SEPARATION AND DIVIDING WALL FRACTIONAL DISTILLATION

FIELD OF THE INVENTION

The invention relates generally to the isomerization of hydrocarbons. More specifically, the invention involves an isomerization zone followed by adsorptive separation of the isomerate into an extract stream and a raffinate stream followed by fractionation of the extract and of the raffinate to recover desorbent and finally further fractionation of the raffinate in a dividing wall fractional distillation column.

BACKGROUND OF THE INVENTION

In many commercially important petrochemical and petroleum industry processes it is desired to separate closely boiling chemical compounds or to perform a separation of chemical compounds by structural class. It is very difficult or impossible to do this by conventional fractional distillation due to the requirement for numerous fractionation columns which may consume excessive amounts of energy. The relevant industries have responded to this problem by utilizing other separatory methods which are capable of performing a separation based upon chemical structure or characteristics. Adsorptive separation is one such method and is widely used to perform these separations.

In the practice of adsorptive separation a feed mixture comprising two or more compounds of different skeletal structure is passed through one or more beds of an adsorbent which selectively adsorbs a compound of one skeletal structure while permitting other components of the feed stream to pass through the adsorption zone in an unchanged condition. The flow of the feed through the adsorbent bed is stopped and the adsorption zone is then flushed to remove nonadsorbed materials surrounding the adsorbent. Thereafter the desired compound is desorbed from the adsorbent by passing a desorbent stream through the adsorbent bed. The desorbent material is commonly also used to flush nonadsorbed materials from the void spaces around and within the adsorbent. This could be performed in a single large bed of adsorbent or in several parallel beds on a swing bed basis. However, it has been found that simulated moving bed adsorptive separation provides several advantages such as high purity and recovery. Therefore, many commercial scale petrochemical separations especially for specific paraffins and xylenes are performed using simulated countercurrent moving bed (SMB) technology.

The passage of the desorbent through the adsorbent dislodges the selectively retained compounds to produce an extract stream. The extract stream contains a mixture of desorbent and the desorbed compounds, with these materials being then separated by distillation in a column referred to as the extract column. The raffinate stream contains a mixture of desorbent and the non-adsorbed compounds, with the desorbent being removed from the raffinate stream by distillation in a column referred to as the raffinate column. The subject invention is aimed at improving the ultimate product of the isomerization process through improving the fractionation employed in recovering the final desired compounds from the raffinate stream.

Several economic advantages are derived from the continuous, as compared to batch-wise, operation of large-scale adsorptive separation processes. Recognition of this has driven the development of simulated moving bed (SMB) adsorptive separation processes. These processes typically employ a rotary valve and a plurality of lines to simulate the countercurrent movement of an adsorbent bed through adsorption and desorption zones. This is depicted, for instance, in U.S. Pat. No. 3,205,166 to D. M. Ludlow, et al. and U.S. Pat. No. 3,201,491 to L. O. Stine et al.

U.S. Pat. No. 3,510,423 to R. W. Neuzil et al. provides a depiction of the customary manner of handling the raffinate and extract streams removed from an SMB process, with the desorbent being recovered, combined and recycled to the adsorption zone. U.S. Pat. No. 4,036,745 describes the use of dual desorbents with a single adsorption zone to provide a higher purity paraffin extract. U.S. Pat. No. 4,006,197 to H. J. Bieser extends this teaching on desorbent recycling to three component desorbent mixtures.

The dividing wall or Petyluk configuration for fractionation columns was initially introduced some 50 years ago by Petyluk et al. A recent commercialization of a fractionation column employing this technique prompted more recent investigations as described in the article appearing at page s14 of a *Supplement to The Chemical Engineer,* Aug. 27, 1992.

The use of dividing wall columns in the separation of hydrocarbons is also described in the patent literature. For instance, U.S. Pat. No. 2,471,134 issued to R. O. Wright describes the use of a dividing wall column in the separation of light hydrocarbons ranging from methane to butane. U.S. Pat. No. 4,230,533 issued to V. A. Giroux describes a control system for a dividing wall column and illustrates the use of the claimed invention in the separation of aromatics comprising benzene, toluene and orthoxylene.

The use of the dividing wall column in the present invention is a significant advantage over isomerization flow schemes that do not employ a dividing wall fractionation column, such as that described in Domergue, B., Watripont, L. *World Refining,* May 2000, p. 26–30.

SUMMARY OF THE INVENTION

One purpose of the invention is to provide a method for separating 2-methylpentane and 3-methylpentane from a mixture containing at least 2-methylpentane, 3-methylpentane, 2,2-dimethylbutane, 2,3-dimethylpentane, isopentane, methylcyclopentane, cyclohexane, and $C_7$+ hydrocarbons. The mixture is introduced into a dividing wall fractionation column operated at fractionation conditions and divided into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column. The mixture is introduced to the column at an intermediate point of the first fractionation zone. A stream of 2-methylpentane and 3-methylpentane is removed from an intermediate point of the second fractionation zone of the dividing wall fractionation column; a stream of, 2,2-dimethylbutane, 2,3-dimethylpentane, and isopentane, is removed from a first end of the dividing wall fractionation column, and a stream of methylcyclopentane, cyclohexane, and $C_7$+ hydrocarbons, is removed from a second end of the dividing wall fractionation column.

A specific embodiment of the invention provides an isomerization process having an adsorptive separation zone and a dividing wall fractionation zone. A feed stream containing at least normal pentane and normal hexane is contacted in an isomerization zone with an isomerization catalyst under isomerization conditions to convert at least a portion of the normal pentane and normal hexane into isomerized products and form an isomerization zone effluent containing normal pentane, normal hexane and isomerized products. This effluent is passed to an adsorptive separation zone comprising a bed of a selective adsorbent maintained at adsorption conditions under which the normal pentane and normal hexane are selectively retained on a quantity of the selective adsorbent, thus forming an isomerized product stream containing at least the isomerized products. The normal pentane and normal hexane are desorbed under desorption conditions to yield a normal alkane stream of at least normal pentane and normal hexane. The isomerized product stream is passed into a dividing wall fractionation column operated at fractionation conditions and divided into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column. The isomerized product stream is introduced at an intermediate point of the first fractionation zone. A low-octane stream of 2-methylpentane and 3-methylpentane is removed from an intermediate point of the second fractionation zone of the dividing wall fractionation column. A first high-octane stream is removed from a first end of the dividing wall fractionation column, and a second high-octane stream is removed from a second end of the dividing wall fractionation column.

Another specific embodiment of the invention provides an isomerization process having an adsorptive separation zone, an integrated fractionation zone, and a dividing wall fractionation zone. A feed stream containing at least normal pentane and normal hexane is contacted with an isomerization catalyst under isomerization conditions in an isomerization zone to convert at least a portion of the normal pentane and normal hexane into isomerized products and form an isomerization zone effluent containing normal pentane, normal hexane and isomerized products. The isomerization zone effluent is passed to an adsorptive separation zone having a bed of a selective adsorbent maintained at adsorption conditions under which the normal pentane and normal hexane are selectively retained on a quantity of the selective adsorbent, thus forming a raffinate stream of the isomerized products and desorbent formerly present in the quantity of the selective adsorbent. Desorbent is contacted with the quantity of the selective adsorbent which has retained the normal pentane and normal hexane under desorption conditions to yield an extract stream of normal pentane, normal hexane, and the desorbent. The extract stream is passed to an integrated fractionation column operated at fractionation conditions and divided into at least a first and a second vertical fractionation zone, with each zone having an upper and a lower end located within the fractionation column, with the first and second fractionation zones being in open communication at their upper ends at a first end of the column and with the extract stream entering the fractionation column at an intermediate point of the first fractionation zone. The raffinate stream is passed into an intermediate point of the second fractionation zone of the integrated fractionation column. An extract product stream is removed from a first end of the first fractionation zone, with the first end not being in communication with the second fractionation zone and being located at the second end of the integrated fractionation column. A raffinate product stream is removed from a first end of the second fractionation zone, with the first end not being in communication with the first fractionation zone and being located at the second end of the integrated fractionation column. A desorbent stream is removed from the first end of the integrated fractionation column. The raffinate product stream is passed to a dividing wall fractionation column operated at fractionation conditions and divided into at least two parallel fractionation zones, Zone A and Zone B, by a dividing wall, with Zone A and Zone B each having an upper and a lower end located within the fractionation column, with Zone A and Zone B being in open communication at their upper ends with an undivided upper section of the fractionation column and in open communication at their lower ends with an undivided lower section of the fractionation column, and with the raffinate product stream entering the column at an intermediate point of Zone A. A lowoctane stream of 2-methylpentane and 3-methylpentane is removed from an intermediate point of Zone B of the dividing wall fractionation column. A first high-octane stream is removed from a first end of the dividing wall fractionation column, and a second high-octane stream is removed from a second end of the dividing wall fractionation column.

DETAILED DESCRIPTION OF THE INVENTION

Figure 1:
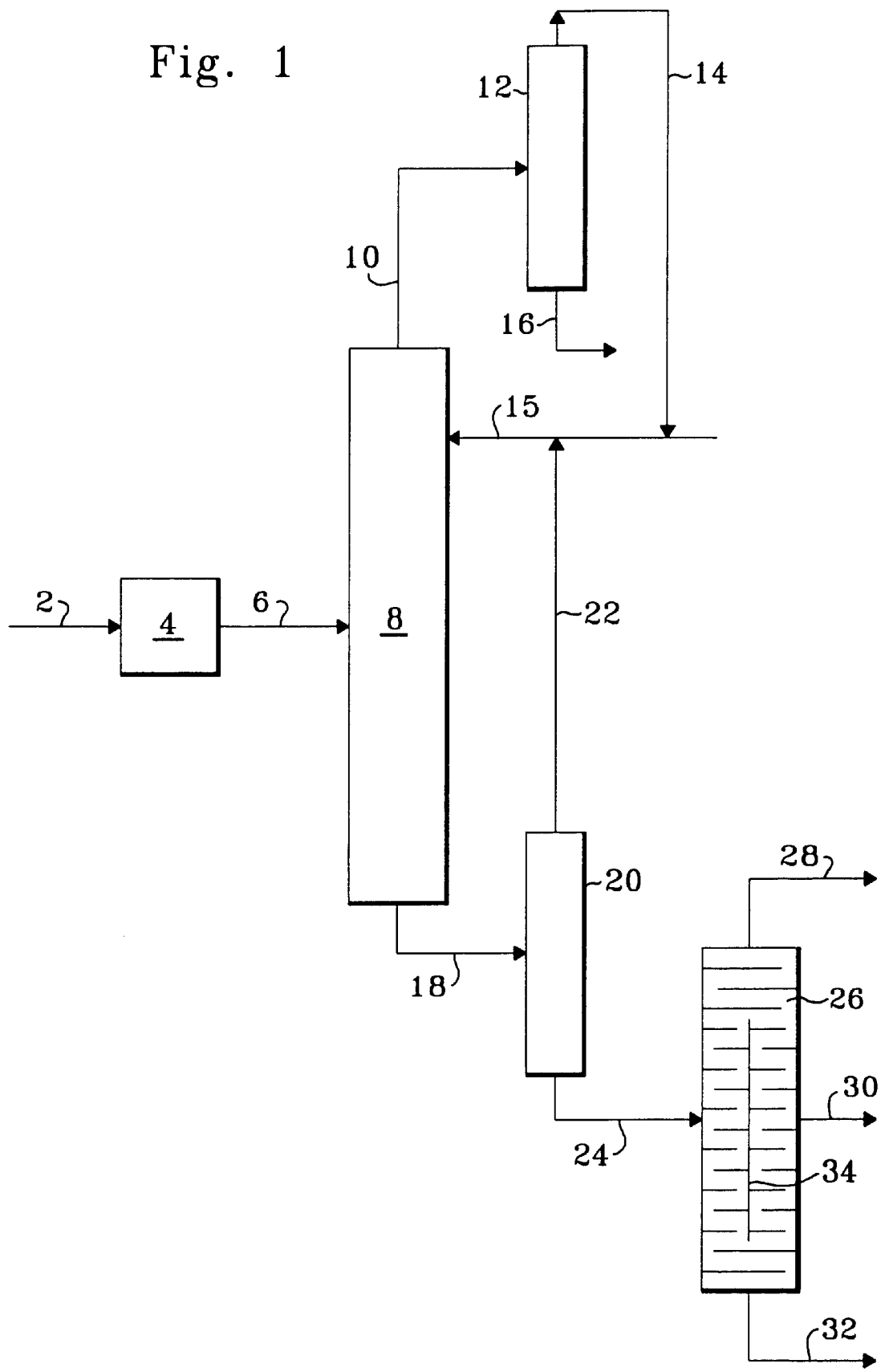
FIG. 1 is a highly simplified process flow diagram of a first embodiment of the invention showing the raffinate stream recovered from a simulated moving bed adsorptive separation zone being passed into a fractionation zone having an extract column and a raffinate column to remove desorbent and form raffinate product with the raffinate product being passed to the left-hand fractionation zone of a single dividing wall product recovery column to separate and recover the high-octane components.

The invention is not restricted to any particular type of isomerization zone or adsorption zone, however the improvement is found in the particular downstream processing of the isomerized products stream (or raffinate), and in another embodiment, both the extract and the raffinate. The isomerization zone and the adsorption zone will be discussed in general terms, and then the improved downstream processing will be discussed.

The isomerization zone can consist of any type of isomerization zone that takes a stream of $C_5$ to $C_6$ straight chain hydrocarbons or a mixture of straight chain and branched chain hydrocarbons and converts straight chain hydrocarbons in the feed mixture to branched chain hydrocarbons and branched chain hydrocarbons to more highly branched chain hydrocarbons thereby producing an effluent having branched chain and straight chain hydrocarbons. In liquid phase operation, the adsorption section is preferably a simulated moving bed, although other schemes for contacting the adsorbent with the feed mixture and desorbing the feed mixture from the adsorbent with the desorbent material may be utilized. In vapor phase operation, the adsorption section may be chosen to be a pressure swing adsorption system, although other adsorptive separation modes could be successfully used. Simulated moving bed will be exemplified throughout most of the detailed description of the invention with an embodiment incorporating the pressure swing adsorption shown in an example.

Suitable feedstocks for the isomerization zone will include $C_5$ and $C_6$ hydrocarbons, and will include at least normal hexane and normal pentane. The typical feed for this process will be a naphtha feed with an initial boiling point in the range of normal butane. The feedstocks that can be used for this invention include hydrocarbon fractionations rich in $C_4$ to $C_6$ normal paraffins. The term "rich" is defined as having a stream having more than 50% of the mentioned component. Useful feedstocks include light natural gasoline, light straight-run naphtha, gas oil condensates, light raffinates, light reformate, light hydrocarbons, and straight-run distillates having distillation end points of about 77° C. (170° F.) and containing substantial quantities of $C_4$ to $C_6$ paraffins. The feed may also contain low concentrations of unsaturated hydrocarbons and hydrocarbons having more than 6 carbon atoms. The concentrations of these materials should be limited to 10 wt. % for unsaturated compounds and 20 wt. % for heavier hydrocarbons in order to restrict hydrogen consumption in cracking reactions. The feed and any normal paraffin recycle are combined and typically enter the isomerization zone with a hydrogen stream. In an alternative embodiment, the feed stream may be introduced to the adsorptive separation zone first to separate and remove any branched hydrocarbons with the normal hydrocarbons being recycled to the isomerization zone.

Hydrogen is admixed with the feed to the isomerization zone in an amount that will provide a hydrogen to hydrocarbon molar ratio of from 0.01 to 10 in the effluent from the isomerization zone. Preferably, the hydrogen to hydrocarbon molar ratio is in the range of 0.05 to 5. Although no net hydrogen is consumed in the isomerization reaction, the isomerization zone will have a net consumption of hydrogen often referred to as the stoichiometric hydrogen requirement which is associated with a number of side reactions that occur. These side reactions include saturation of olefins and aromatics, cracking and disproportionation. For feeds having a high level of unsaturates, satisfying the stoichiometric hydrogen will require a higher hydrogen to hydrocarbon molar ratio for the feed at the inlet of the isomerization zone. Hydrogen in excess of the stoichiometric amounts for the side reactions is often maintained in the reaction zone to provide stability and conversion by compensating for variation in feed stream compositions that alter the stoichiometric hydrogen requirements. Higher hydrogen to hydrocarbon molar ratios are often used to prolong catalyst life by suppressing side reactions such as cracking and disproportionation. When such side reactions occur, they can reduce conversion and lead to formation of carbonaceous compounds, usually referred to as coke, that foul the catalyst.

It has been found that the hydrogen to hydrocarbon ratio in isomerization zones that use a chlorided platinum alumina catalyst can be reduced significantly. In such cases, it is desirable to reduce the amount of hydrocarbon that enters the isomerization zone such that the hydrogen to hydrocarbon molar ratio of the effluent from the isomerization zone is less than 0.05. Reduced hydrogen to hydrocarbon molar ratios have been used based on the finding that the amount of hydrogen needed for suppressing coke formation need not exceed dissolved hydrogen levels. The amount of hydrogen in solution at the normal conditions of the isomerization zone effluent is preferably in a molar ratio of from 0.02 to 0.01. The amount of excess hydrogen over the stoichiometric requirement that is required for good stability and conversion is in a molar ratio of 0.01 to less than 0.05.

When the hydrogen to hydrocarbon molar ratio exceeds 0.05, it is not economically desirable to operate the isomerization zone without the recycle of hydrogen to the isomerization zone. Therefore, in such cases, recovery facilities for hydrogen from the effluent will be provided as hereinafter described. Hydrogen may be added to the feed mixture in any manner that provides the necessary control for the addition of the hydrogen.

The hydrogen and hydrocarbon feed mixture is contacted in the reaction zone with an isomerization catalyst. The catalyst composites that can be used in the isomerization zone include traditional isomerization catalysts. Such catalysts include high chloride catalyst on an alumina base containing platinum, and crystalline aluminosilicates or crystalline zeolites. Suitable catalyst compositions of this type will exhibit selective and substantial isomerization activity under the operating conditions of the process.

The preferred isomerization catalyst for this invention is a chlorided platinum alumina catalyst. The alumina is preferably an anhydrous gamma-alumina with a high degree of purity. The catalyst may also contain other platinum group metals. The term "platinum group metals" refers to noble metals excluding silver and gold which are selected from the group consisting of platinum, palladium, germanium, ruthenium, rhodium, osmium, and iridium. These metals demonstrate differences in activity and selectivity such that platinum has now been found to be the most suitable for this process. The catalyst will contain from about 0.1 to 0.25 wt. % of the platinum. Other platinum group metals may be present in a concentration of from 0.1 to 0.25 wt. %. The platinum component may exist within the final catalytic composite as an oxide or halide or as an elemental metal. The presence of the platinum component in its reduced state has been found most suitable for this process. The chloride component termed in the art "a combined chloride" is present in an amount from about 2 to about 15 wt. % based upon the dry support material. The use of chloride in amounts greater than 5 wt. % have been found to be the most beneficial for this process. The inorganic oxide preferably comprises alumina and more preferably gamma-alumina, eta-alumina, and mixtures thereof.

There are a variety of ways for preparing the catalytic composite and incorporating the platinum metal and the chloride therein. The method that has shown the best results in this invention prepares the catalyst by impregnating the carrier material through contact with an aqueous solution of a water-soluble decomposable compound of the platinum group metal. For best results, the impregnation is carried out by dipping the carrier material in a solution of chloroplatinic acid. Additional solutions that may be used include ammonium chloroplatinate, bromoplatinic acid or platinum dichloride. Use of the platinum chloride compound serves the dual function of incorporating the platinum component and at least a minor quantity of the chloride into the catalyst. Additional amounts of halogen must be incorporated into the catalyst by the addition or formation of aluminum chloride to or on the platinum-aluminum catalyst base. An alternate method of increasing the halogen concentration in the final catalyst composite is to use an aluminum hydrosol to form the aluminum carrier material such that the carrier material also contains at least a portion of the chloride. Halogen may also be added to the carrier material by contacting the calcined carrier material with an aqueous solution of the halogen acid such as hydrogen chloride.

It is generally known that high chlorided platinum-alumina catalysts of this type are highly sensitive to sulfur and oxygen-containing compounds. Therefore, the use of such catalysts requires that the feedstock be relatively free of such compounds. A sulfur concentration no greater than 0.5 ppm is generally required. The presence of sulfur in the feedstock serves to temporarily deactivate the catalyst by platinum poisoning. Activity of the catalyst may be restored by hot hydrogen stripping of sulfur from the catalyst composite or by lowering the sulfur concentration in the incoming feed to below 0.5 ppm so that the hydrocarbon will desorb the sulfur that has been adsorbed on the catalyst. Water can act to permanently deactivate the catalyst by removing high activity chloride from the catalyst and replacing it with inactive aluminum hydroxide. Therefore, water, as well as oxygenates, in particular $C_1$–$C_5$ oxygenates, that can decompose to form water, can only be tolerated in very low concentrations. In general, this requires a limitation of oxygenates in the feed to about 0.1 ppm or less. The feedstock may be treated by any method that will remove water and sulfur compounds. Sulfur may be removed from the feed stream by hydrotreating. A variety of commercial dryers are available to remove water from the feed components. Adsorption processes for the removal of sulfur and water from hydrocarbon streams are also well known to those skilled in the art.

As a class, the crystalline aluminosilicate or crystalline zeolite catalysts comprise crystalline zeolitic molecular sieves having an apparent pore diameter large enough to adsorb neopentane A silica alumina molar ratio $SiO_2$:$Al_2O_3$ of greater than 3, less than 60 and preferably between 15 and 30 is desirable. In preferred form, the zeolite will contain an equivalent percentage of alkali metal cations and will have those $AlO_4$-tetrahedra not associated with alkali metal cations, either not associated with any metal cations or associated with divalent or other polyvalent metal cations. Usually the molecular sieve is a mordenite molecular sieve which is essentially in the acid form or is converted to the acid form. Particularly preferred catalysts of this type for isomerization are disclosed in detail in U.S. Pat. Nos. 3,442,794 and 3,836,597.

A preferred composition of zeolitic catalyst for use in the present invention comprises a Group VIII noble metal, a hydrogen form crystalline aluminosilicate, and a refractory inorganic oxide with the catalyst composition having a surface area of at least 580 m²/g. Significant improvements in isomerization performance are realized when the surface area of the catalytic composite is at or above 580 m²/g. A Group VIII metal is incorporated into the catalytic composite to supply a hydrogenation/dehydrogenation function and the preferred Group VIII noble metal is platinum. The Group VIII noble metal is present in an amount from about 0.01 to 5% by weight of the composite and preferably in an amount of at least 0.15% by weight but not over 0.35% by weight. The zeolitic catalytic composite may also contain a cata-lytically effective amount of a promoter metal such as tin, lead, germanium, cobalt, nickel, iron, tungsten, chromium, molybdenum, bismuth, indium, gallium, cadmium, zinc, uranium, copper, silver, gold, tantalum, or one or more of rare earth metals and mixtures thereof. The hydrogen-formed silica alumina has either a three-dimensional or channel pore structure crystal lattice framework. The three-dimensional aluminosilicates include both synthetic and naturally occurring silica aluminas such as faujasites, which include X-type, Y-type, ultrastable-Y, and the like. L-type, omega-type, and mordenite are examples of the channel pore structure crystalline aluminosilicates. Mordenite in either naturally occurring or synthetic form is preferred, particularly with a silica to alumina ratio of at least 16:1. The hydrogen form aluminosilicate may be present in an amount within the range of 50 to about 99.5 wt. %, preferably within the range of 75 to about 95 wt. %, and a refractory inorganic oxide may be present in an amount within the range of from 25 to about 50 wt. %.

Operating conditions within the isomerization zone are selected to maximize the production of isomerized product from the feed components. Temperatures within the reaction zone will usually range from about 40–320° C. (100°–600° F.). Lower reaction temperatures are generally preferred since they usually favor equilibrium mixtures of isomerized products versus normal alkanes. Lower temperatures are particularly useful in processing feeds composed of $C_5$ and $C_6$ alkanes where the lower temperatures favor equilibrium mixtures having the highest concentration of the most branched isoalkanes. When the feed mixture is primarily $C_5$ and $C_6$ alkanes, temperatures in the range of from 60° to 160° C. are preferred. Higher reaction temperatures increase catalyst activity and promote the isomerization of $C_4$ hydrocarbons. The reaction zone may be maintained over a wide range of pressures. Pressure conditions in the isomerization of $C_4$–$C_6$ paraffins range from 700 to 7000 Kpag. Preferred pressures for this process are in the range of from 2000 to 3000 Kpag. The feed rate to the reaction zone can also vary over a wide range. These conditions include liquid hourly space velocities ranging from 0.5 to 12 hr.$^{-1}$, however, space velocities between 1 and 6 hr.$^{-1}$ are preferred. The isomerization zone will usually operate at a LHSV of about 1 to about 2.

Operation of the isomerization zone with the preferred chlorided platinum-alumina catalyst also requires the presence of a small amount of an organic chloride promoter. The organic chloride promoter serves to maintain a high level of active chloride on the catalyst as low levels are continuously stripped off the catalyst by the hydrocarbon feed. The concentration of promoter in the reaction zone is typically maintained at from 30 to 300 ppm. The preferred promoter compound is perchloroethylene. Other suitable promoter compounds include oxygen-free decomposable organic chlorides such as propyldichloride, butylchloride, and chloroform to name only a few of such compounds. The need to keep the reactants dry is reinforced by the presence of the organic chloride compound which converts to hydrogen chloride. As long as the process streams are kept dry, there will be no adverse effect from the presence of hydrogen chloride.

The isomerization zone usually includes a two-reactor system with a first stage reactor and a second stage reactor with the catalyst being distributed equally between the two reactors. It is not necessary that the reaction is carried out in two reactors but the use of two reactors confer several benefits on the process. The use of two reactors and specialized valving allows partial replacement of the catalyst system without taking the isomerization unit off stream. For the short periods of time during which replacement of catalyst may be necessary, the entire flow of reactants may be processed through only one reaction vessel while catalyst is replaced in the other. The use of two reaction zones also aids in maintaining lower catalyst temperatures. This is accomplished by having any exothermic reaction such as hydrogenation of unsaturates performed in a first reaction vessel with the rest of the reaction carried out in a final reaction vessel at more favorable temperature conditions.

The effluent from the reactors enters a stabilizer that removes light gases and butane from the effluent (not shown). The amount of butane taken off from the stabilizer will vary depending upon the amount of butane entering the process. The stabilizer normally runs at a pressure of from 800 to 1700 Kpaa. When the isomerization zone is operated with a high hydrogen to hydrocarbon ratio, a separator is usually placed ahead of the stabilizer. A hydrogen-rich recycle gas stream is recovered from the separator and recycled for combination with the feed entering the isomerization zone. When the isomerization zone operates with very low hydrogen to hydrocarbon ratios the separator is not needed and the effluent from the isomerization zone may enter the stabilizer directly.

The bottoms stream from the stabilizer provides an isomerization zone effluent stream comprising $C_5$ and higher boiling hydrocarbons that include normal paraffins for recycle and branched isomerized products. The chlorides which may be present in the reaction zone will usually pose no problem for the sorbent in the adsorption zone. In normal operation, any chlorides that are present in the effluent from the isomerization zone will be removed in the overhead from the stabilizer. However, where the isomerization zone or separators downstream from the isomerization zone are subject to upsets, it may be desirable to provide a guard bed of some type to treat the stabilizer bottoms and prevent any carryover of chloride compounds into the adsorption section.

The isomerization effluent is taken by line 6 and enters the adsorptive separation zone 8 where it is contacted with an adsorbent. It is expected that the isomerization effluent will contain compounds such as normal pentane, normal hexane, methylpentane, 2-methylpentane, 3-methylpentane, methylcyclopentane, $C_7+$, isopentane, 2,2-dimethylbutane, 2,3-dimethylbutane, perhaps some butane and butanes, and trace other compounds. The adsorption section of this invention is operated to primarily remove the normal pentane and normal hexane fraction from the effluent of the isomerization zone. This process is especially suited for adsorption systems that use multiple ports for supplying the process streams to the adsorbent and divide the adsorbent into a plurality of zones for adsorbing normal paraffins, recovering isoparaffins, purifying the adsorbent, and desorbing the normal paraffins. A well-known process of this type is the simulated countercurrent moving bed system for simulating moving bed countercurrent flow systems as described earlier. Additional details on the operation of a typical adsorption zone in an isomerization application may be found in U.S. Pat. No. 5,043,525 hereby incorporated by reference in its entirety.

Although much of the description herein is set in terms of use of the invention in an SMB process, the invention is believed applicable to other modes of performing adsorptive separation such as a swing bed system employing one or more separate beds of adsorbent. The greatest benefit of the present invention is as applied to an adsorptive separation process that produces a stream comprising three compounds that are to be separated by fractionation. An example is provided below describing a specific embodiment of the invention that employs a pressure swing adsorption zone. Another variation in the simulated moving bed performance of the process is the replacement of the rotary valve with a manifold system of valves. Such systems have been described in the art such as U.S. Pat. No. 4,434,051, and become more practical as the number of sub-beds of adsorbent decreases. For liquid phase operation, a simulated moving bed is preferred, and will be discussed in detail below. For vapor phase operation, a pressure swing adsorption zone may be employed (see FIG. 3).

A number of specially defined terms are commonly used in describing the simulated moving bed processes. The term "feed stream" indicates a stream in the process through which feed material passes to the molecular sieve. A feed material comprises one or more extract components and one or more raffinate components. An "extract component" is a compound or type of compound that is more selectively retained by the molecular sieve while a "raffinate component" is a compound or type of compound that is less selectively retained. In this process normal hydrocarbons from the feed stream are extract components while isomerized products and feed stream branched chain and cyclic hydrocarbons are raffinate components. The term "displacement fluid" "or desorbent" shall mean generally a material capable of displacing an extract component. The term "desorbent" or "desorbent input stream" indicates the stream through which desorbent passes to the molecular sieve. The term "raffinate stream" or "raffinate output stream" means a stream through which most of the raffinate components are removed from the molecular sieve. The composition of the raffinate stream can vary from about 100% desorbent to essentially 100% raffinate components. The term "extract stream" or "extract output stream" means a stream through which an extract material which has been displaced by a desorbent is removed from the molecular sieve. The composition of the extract stream can also vary from about 100% desorbent to essentially 100% extract components.

Desorbent is also introduced to adsorptive separation zone 8 via line 15. For this specific embodiment, the preferred desorbent is a mixture of normal butane and isobutane. The ratio of normal butane to isobutane in a desorbent mixture preferably is in the range of from about 80:20 to about 95:5. As an option line 15 and line 6 may be combined and fed to the adsorptive separation section 8 in combination. However, it is preferred to introduce the desorbent in a separate stream so as to control the location of the desorbent input into the simulated moving bed.

Operating conditions for adsorption include, in general, a temperature range of from about 20 to about 250° C., with from about 60 to about 200° C. being preferred. Temperatures from 90° C. to 160° C. are highly preferred for the second adsorption zone. Adsorption conditions also preferably include a pressure sufficient to maintain the process fluids in liquid phase; which may be from about atmospheric to 600 psig. Desorption conditions generally include the same temperatures and pressure as used for adsorption conditions. It is generally preferred that an SMB process is operated with an A:F flow rate through the adsorption zone in the broad range of about 1:1 to 5:1.0 where A is the volume rate of "circulation" of selective pore volume in the adsorbent and F is the feed flow rate. The practice of the subject invention requires no significant variation in operating conditions, adsorbent or desorbent composition within the adsorbent chambers. That is, the adsorbent preferably remains at the same temperature throughout the process.

The success of a particular adsorptive separation is determined by many factors. Predominant in these factors are the composition of the adsorbent (stationary phase) and desorbent (mobile phase) employed in the process. The remaining factors are basically related to process conditions.

The subject process is not believed to be limited to use with any particular form of adsorbent. The adsorbents employed in the process preferably comprise a molecular sieve such as a type A, X or Y zeolite or silicalite. Silicalite is well described in the literature. It is disclosed and claimed in U.S. Pat. No. 4,061,724 issued to Grose et al. A more detailed description is found in the article, "Silicalite, A New Hydrophobic Crystalline Silica Molecular Sieve," Nature, Vol. 271, Feb. 9, 1978 which is incorporated herein by reference for its description and characterization of silicalite. Silicalite is a hydrophobic crystalline silica molecular sieve having intersecting bent-orthogonal channels formed with two cross-sectional geometries, 6 Å circular and 5.1–5.7 Å elliptical on the major axis. A wide number of adsorbents are known and a starting molecular sieve is often treated by ion exchange or steaming etc to adjust its adsorptive properties. Adsorbents based upon zeolites X and Y are described in more detail in U.S. Pat. Nos. 3,663,638; 3,626,020 and 3,997,620.

The active component of the adsorbents is normally used in the form of particle agglomerates having high physical strength and attrition resistance. The agglomerates contain the active adsorptive material dispersed in an amorphous, inorganic matrix or binder, having channels and cavities therein which enable fluid to access the adsorptive material. Methods for forming the crystalline powders into such agglomerates include the addition of an inorganic binder, generally a clay comprising a silicon dioxide and aluminum oxide, to a high purity adsorbent powder in a wet mixture. The binder aids in forming or agglomerating the crystalline particles. The blended clay-adsorbent mixture may be extruded into cylindrical pellets or formed into beads which are subsequently calcined in order to convert the clay to an amorphous binder of considerable mechanical strength. The adsorbent may also be bound into irregular shaped particles formed by spray drying or crushing of larger masses followed by size screening. The adsorbent particles may thus be in the form of extrudates, tablets, spheres or granules having a desired particle range, preferably from about 16 to about 60 mesh (Standard U.S. Mesh) (1.9 mm to 250 microns). Clays of the kaolin type, water permeable organic polymers or silica are generally used as binders.

The active molecular sieve component of the adsorbents will ordinarily be in the form of small crystals present in the adsorbent particles in amounts ranging from about 75 to about 98-wt. % of the particle based on volatile-free composition. Volatile-free compositions are generally determined after the adsorbent has been calcined at 900° C. in order to drive off all volatile matter. The remainder of the adsorbent will generally be the inorganic matrix of the binder present in intimate mixture with the small particles of the silicalite material. This matrix material may be an adjunct of the manufacturing process for the silicalite, for example, from the intentionally incomplete purification of the silicalite during its manufacture.

Those skilled in the art will appreciate that the performance of an adsorbent is often greatly influenced by a number of factors not related to its composition such as operating conditions, feed stream composition and the water content of the adsorbent. The optimum adsorbent composition and operating conditions for the process are therefore dependent upon a number of interrelated variables. One such variable is the water content of the adsorbent which is expressed herein in terms of the recognized Loss on Ignition (LOI) test. In the LOI test the volatile matter content of the zeolitic adsorbent is determined by the weight difference obtained before and after drying a sample of the adsorbent at 500° C. under an inert gas purge such as nitrogen for a period of time sufficient to achieve a constant weight. For the subject process it is preferred that the water content of the adsorbent results in an LOI at 900° C. of less than 7.0% and preferably within the of from 0 to 4.0 wt. %. As the process fluids may dry the adsorbent, the hydration level of the sieve is normally controlled by controlled water injection, as via the desorbent stream.

An important characteristic of an adsorbent is the rate of exchange of the desorbent for the extract component of the feed mixture materials or, in other words, the relative rate of desorption of the extract component. This characteristic relates directly to the amount of desorbent material that must be employed in the process to recover the extract component from the adsorbent. Faster rates of exchange reduce the amount of desorbent material needed to remove the extract component and therefore, permit a reduction in the operating cost of the process. With faster rates of exchange, less desorbent material has to be pumped through the process and separated from the extract stream for reuse in the process. Exchange rates are often temperature dependent. Ideally, desorbent materials should have a selectivity equal to about 1 or slightly less than 1 with respect to all extract components so that all of the extract components can be desorbed as a class with reasonable flow rates of desorbent material, and so that extract components can later displace desorbent material in a subsequent adsorption step.

In adsorptive separation processes, which are generally operated continuously at substantially constant pressures and a temperature which ensures liquid phase, the desorbent material must be judiciously selected to satisfy many criteria. First, the desorbent material should displace an extract component from the adsorbent with reasonable mass flow rates without itself being so strongly adsorbed as to unduly prevent an extract component from displacing the desorbent material in a following adsorption cycle. Expressed in terms of the selectivity, it is preferred that the adsorbent be more selective for all of the extract components with respect to a raffinate component than it is for the desorbent material with respect to a raffinate component. Secondly, desorbent materials must be compatible with the particular adsorbent and the particular feed mixture. More specifically, they must not reduce or destroy the capacity of the adsorbent or selectivity of the adsorbent for an extract component with respect to a raffinate component. Additionally, desorbent materials should not chemically react with or cause a chemical reaction of either an extract component or a raffinate component. Both the extract stream and the raffinate stream are typically removed from the adsorbent void volume in admixture with desorbent material and any chemical reaction involving a desorbent material and an extract component or a raffinate component or both would complicate or prevent product recovery. The desorbent should also be easily separated from the extract and raffinate components, as by fractionation. Finally, desorbent materials should be readily available and reasonable in cost.

Further details on equipment and techniques for use in an SMB process may be found in U.S. Pat. Nos. 3,208,833; 3,214,247; 3,392,113; 3,455,815; 3,523,762; 3,617,504; 3,686,342; 4,006,197; 4,133,842; 4,434,051 and 5,177,295, which are incorporated herein by reference for this teaching. A different type of simulated moving bed operation which can be performed using similar equipment, adsorbent and conditions but which simulates cocurrent flow of the adsorbent and liquid in the adsorption chambers is described in U.S. Pat. Nos. 4,402,832 and 4,498,991.

A related SMB processing technique is the use of "zone flush." The zone flush forms a buffer zone between the feed and extract bed lines to keep the desorbent, e.g., normal pentane, from entering the adsorption zone. While the use of a zone flush requires a more complicated, and thus more costly rotary valve, the use of zone flush is preferred in the adsorption zones when high purity extract products are desired. In practice, a quantity of the mixed component desorbent recovered overhead from the extract and/or raffinate columns is passed into a separate splitter column. A high purity stream of the lower strength component of the mixed component desorbent is recovered and used as the zone flush stream. Further information on the use of dual component desorbents and on techniques to improve product purity such as the use of flush streams may be obtained from U.S. Pat. Nos. 3,201,491; 3,274,099; 3,715,409; 4,006,197 and 4,036,745 which are incorporated herein by reference for their teaching on this aspect of SMB technology.

SMB Technology has been applied to a wide variety of chemicals in addition to those described above. For instance, U.S. Pat. No. 4,467,126 describes the recovery of a di-substituted benzene such as a nitrotoluene isomer. The separation of 2,6-dimethylnaphthalene is described in U.S. Pat. No. 5,004,853 and 2,7-diisopropylnapthalene in U.S. Pat. No. 5,012,039. SMB technology has been extended to the separation of sugars, to the separation of chiral compounds and to more complicated organics such as fatty acids and triglycerides as described in U.S. Pat. No. 5,225,580. The separation of fatty acids is described in U.S. Pat. Nos. 4,404,145; 4,770,819; 5,171,870 and 5,179,219. It is believed that the subject process can be applied to any such SMB process requiring desorbent recovery from extract or raffinate components, especially when a third component separable by fractionation is also present.

It has become customary in the art to group the numerous beds in the SMB adsorption chamber(s) into a number of zones. Usually the process is described in terms of 4 or 5 zones. The first contact between the feed stream and the adsorbent is made in Zone I, the adsorption zone. The adsorbent or stationary phase in Zone I becomes surrounded by liquid which contains the undesired isomer(s), that is, with raffinate. This liquid is removed from the adsorbent in Zone II, referred to as a purification zone. In the purification zone the undesired raffinate components are flushed from the void volume of the adsorbent bed by a material which is easily separated from the desired component by fractional distillation. In Zone III of the adsorbent chamber(s) the desired isomer is released from the adsorbent by exposing and flushing the adsorbent with the desorbent (mobile phase). The released desired component and accompanying desorbent are removed from the adsorbent in the form of the extract stream. Zone IV is a portion of the adsorbent located between Zones I and III which is used to segregate Zones I and III. In Zone IV desorbent is partially removed from the adsorbent by a flowing mixture of desorbent and undesired components of the feed stream. The liquid flow through Zone IV prevents contamination of Zone III by Zone I liquid by flow cocurrent to the simulated motion of the adsorbent from Zone III toward Zone I. A more thorough explanation of simulated moving bed processes is given in the Adsorptive Separation section of the Kirk-Othmer Encyclopedia of Chemical Technology at page 563. The terms "upstream" and "downstream" are used herein in their normal and are interpreted based upon the overall direction in which liquid is flowing in the adsorbent chamber. That is, if liquid is generally flowing downward through a vertical adsorbent chamber, then upstream is equivalent to an upward or higher location in the chamber.

The extract stream is directed to an extract fractionation column where an extract product comprising primarily normal pentane and normal hexane is separated from the desorbent which is a mixture of normal butane and isobutane. A desorbent drag stream may be removed from the fractional distillation column in order to control the ratio of isobutane to normal butane in a desorbent which is recycled to the selective adsorptive separation section. The desorbent drag stream may be employed to remove any excess desorbent components which enter the adsorptive system as part of the feed. It is also feasible to withdraw the drag stream from the raffinate fractionation column in some circumstances. The extract fractionation column typically operates in the range of from about 90 to about 160° C., with the temperature being measured at the bottoms of the column, and from about 50 to about 150 psig, with from about 40 to about 60 trays. The separated desorbent may be recycled to the adsorptive separation zone and the separated extract product stream may be recycled to the isomerization zone.

The raffinate stream from the adsorptive separation zone is directed to a raffinate fractionation column to separate desorbent from isomerized products. Desorbent is removed from the overhead and may be combined with the overhead desorbent from the extract fractionation column and the collective recovered desorbent may be recycled to the adsorptive separation zone. The raffinate product stream is withdrawn from the bottom of the raffinate fractionation column and contains primarily 2,3-dimethylbutane, 2,2-dimethylbutane, isopentane, 2-methylpentane, 3-methylpentane, methylcyclopentane, cyclohexane and $C_7+$. The raffinate fractionation column typically operates in the range of from about 90 to about 160° C., with the temperature being measured at the bottoms of the column, and from about 50 to about 150 psig, with from about 40 to about 60 trays.

The raffinate product stream is directed to an octane enhancement zone having a dividing wall fractional distillation column. Within the dividing wall fractional distillation column are two parallel fractionation zones. A first fractionation zone occupies a large portion of the left-hand side of the mid-section of the fractional distillation column. Note that the terms "left-hand" and "right-hand" are used herein as relative to the drawings. In actual practice the placement of the zones as to the left side or the right side of the column is not critical. This first fractionation zone is separated from a parallel second fractionation zone occupying the other half of the column cross section by a substantially fluid tight vertical wall. The vertical wall is not necessarily centered in the column and the two fractionation zones may differ in cross sectional area or shape. The vertical wall divides a large vertical portion of the column into two parallel fractionation zones. The two zones are isolated from each other for the height of this wall, but communicate at both the top and bottom ends of the column. There is no direct vapor or liquid flow between the two fractionation zones through the dividing wall, but the upper end of the fractionation zone receiving the raffinate product is open to the internal volume of the distillation column containing an undivided fractionation zone preferably having additional trays. Liquid may pass under the dividing wall at the bottom of the two fractionation sections although vapor flow is preferably restricted. Thus, vapor and liquid can freely move around the wall between the two portions of the column. During operation, the raffinate product is separated in the first fractionation zone with the more volatile compounds moving upward out of the left-hand first fractionation zone and emerging into the undivided upper portion of the distillation column. As with the first fractionation zone, the upper end of the right-hand second zone is in open communication with the upper section of the distillation column which preferably contains additional fractionation trays extending across the entire column cross section.

The raffinate product stream contains 2,3-dimethylbutane, 2,2-dimethylbutane, isopentane, 2-methylpentane, 3-methylpentane, methylcyclopentane, cyclohexane and $C_7+$. For ease of discussion, the raffinate product stream components will be grouped according to boiling point, which is the main factor in determining their behavior in the factional distillation column. The components having relatively low boiling points will be labeled Group A and will consist of 2,3-dimethylbutane, 2,2-dimethylbutane, and isopentane. Group A contains high-octane components which are desired products of the overall isomerization process. The mid-range boiling components will be labeled Group B and contains 2-methylpentane and 3-methylpentane. Group B contains lower octane components that would best be recycled to the isomerization zone and not included in a final product (or used in desorbing the normal alkanes in a pressure swing adsorption zone). Separating and recycling the 2-methylpentane and 3-methylpentane results in the final product having a higher overall octane value. The components having relatively high boiling points will be labeled Group C and will consist of methylcyclopentane, cyclohexane, and $C_7+$. Group C also contains high-octane components and are desired products of the overall isomerization process. The combination of Group A and Group C forms the final high-octane isomerization process product.

The raffinate product stream from the raffinate column is introduced into a first vertical fractionation zone occupying a large portion of the left-hand side of the midsection of the fractional distillation column. The Group A components along with a portion of the Group B components present in the raffinate stream are driven upward in the first fractionation zone and enter the top of the column. The top of the column is a purification zone which is designed to separate the Group A components from the group B components. A Group A-rich stream is removed from the top of the dividing wall and passed through an overhead condenser (not shown) to form liquid delivered to the receiver. A liquid phase stream of Group A components is removed from the receiver and divided into a first portion which is returned to the top of the dividing wall fractionation column as reflux and a second portion which is removed from the process. As used herein the term "rich" is intended to indicate a concentration of the indicated compound or class of compounds greater than 50 and preferably greater than 75 mol percent.

The bottom of the dividing wall column also comprises an undivided fractionation zone. This zone can receive liquid draining from both the first and second fractionation zones. This liquid is subjected to fractional distillation which drives the Group B components upwards as vapor while concentrating the less volatile Group C components into a bottoms liquid that is removed from the dividing wall fractionation column. This separation is effected through the use of a reboiler (not shown) providing vapor to the bottom undivided fractionation zone. The Group C-rich bottoms liquid is combined with the Group A rich stream from the top of the column to form the overall isomerization process high-octane product. The Group B components are withdrawn from the dividing wall fractionation column in a side draw from the right-hand side fractionation zone. The Group B components may be recycled to the isomerization zone for isomerization into components having a higher octane value.

In a more specific embodiment of the invention, the undivided bottom section of the dividing wall fractionation column is depicted as separated from the two parallel fractionation zones by a gas flow control or gas trap out tray located just below the bottom of the wall. A slight gap at this point allows horizontal liquid flow between the parallel fractionation zones. This tray may have liquid sealed perforations allowing the normal downward flow of liquid, but its structure is such that the upward flow of vapor is at least greatly restricted. The tray may totally block the upward vapor flow. The use of this tray is preferred as it provides a means to positively control the division of the upward gas flow between the two fractionation zones, which is a prime means of controlling performance of the two zones. The total vapor flow is, therefore, preferably removed from the column via a line and divided between two separate lines which feed the vapor to the bottom of the two parallel fractionation zones. The gas flow may be controlled by one or more flow control valves or by adjusting the relative liquid levels in the bottom of the two zones. This is described in some detail in previously cited U.S. Pat. No. 4,230,533 for a slightly different arrangement.

A representative comparison of the separation as shown in FIG. 1 based solely upon engineering design calculations, which for the conventional case have the benefit of comparison to many operating units, indicates that a conventional fractionation column, commonly referred to as a deisohexanizer, which contains a total of 80 trays could be replaced with the dividing wall column of the present invention containing a total of 65 trays. The dividing wall column requires a total reboiling duty of $3.43 \times 10^7$ BTU/hr versus $5.45 \times 10^7$ BTU/hr for the conventional column. The dividing wall column requires a total condenser duty of $3.99 \times 10^7$ MMBTU/hr versus $6.20 \times 10^7$ for the standard column case. Therefore, the present invention, through the use of the dividing wall column reduces the capital costs as to the number of trays as well as the utility costs as compared to a conventional fractionation column.

An embodiment of the invention may by exemplified by FIG. 1. Reference to the specific arrangement for this invention for the specific embodiment of the invention is not meant to limit the scope to the details disclosed therein. Furthermore, FIG. 1 is a schematic illustration and does not show a number of details for the process arrangement such as pumps, compressors, valves, stabilizers and recycle lines which are well known to those skilled in the art. Feed is conducted via line 2 to isomerization zone 4, both of which are as described in detail above. Isomerization zone effluent is conducted via line 6 to an adsorptive separation zone 8, which is as described in detail above. Recycled and fresh desorbent, a mixture of normal butane and isobutane, is conducted to adsorptive separation zone 8 via line 15. The preferred mode of operation of adsorptive separation zone 8 is a simulated moving bed, however, for ease of understanding, FIG. 1 shows a simplified simulated moving bed, i.e., the rotary valve and sub-beds are not shown. An alternative mode of operation of adsorptive separation zone 8 is pressure swing adsorption, which may involve multiple beds (see FIG. 3 which is discussed below). An extract stream containing normal alkanes and desorbent is removed from adsorptive separation zone 8 via line 10. A raffinate stream containing isomerized products and C7+ hydrocarbons is removed from adsorptive separation zone via line 18.

The extract stream in line 10 is passed to an extract debutanizer column 12 and a desorbent stream 14 is separated from an extract product stream 16 by fractionation. Extract product stream 16 contains normal pentane and normal hexane and may be recycled to the isomerization zone 4 for the production of more desired components. Desorbent stream 14 may be combined with line 15 and recycled to adsorptive separation zone 8. The raffinate stream in line 18 is passed to a raffinate debutanizer column and a desorbent stream 22 is separated from a raffinate product stream 24 by fractionation. The desorbent stream 22 may be combined with line 15 and recycled to adsorptive separation zone 8.

The raffinate product line 24 is Introduced at the midsection of the left-hand side, or first fractionation zone, of dividing wall fractionation column 26 having dividing wall 34. The dimethylbutanes and isopentane along with a portion of the monomethylpentanes are driven upward in the first fractionation zone and enter the top of column 26. A stream rich in dimethylbutanes and isopentane is removed from the top of the dividing wall column 26 in line 28. Line 28 may be passed through an overhead condenser (not shown) to form liquid delivered to the receiver. A liquid phase stream is removed from the receiver and divided into a first portion which is returned to the top of the dividing wall fractionation column as reflux and a second portion which is removed from the process (not shown).

Methylcyclopentane, cyclohexane, and $C_7+$ compounds and some monomethylpentanes drain down the first fractionation zone and enter the bottom of column 26. The monomethylpentanes are driven up into the second fractionation section. A stream rich in methylcyclopentane, cyclohexane, and $C_7+$ compounds is removed from the bottom of the dividing wall column 26 in line 32. A stream containing 2-methylpentane and 3-methylpentane is withdrawn from the dividing wall fractionation column in a side draw from the right-hand side, or second, fractionation zone in line 30. The monomethylpentanes in line 30 may be recycled to the isomerization zone for isomerization into components having a higher octane value. The stream in line 28 may be combined with the stream in line 32 to form the overall isomerization process high-octane product.

Figure 2:
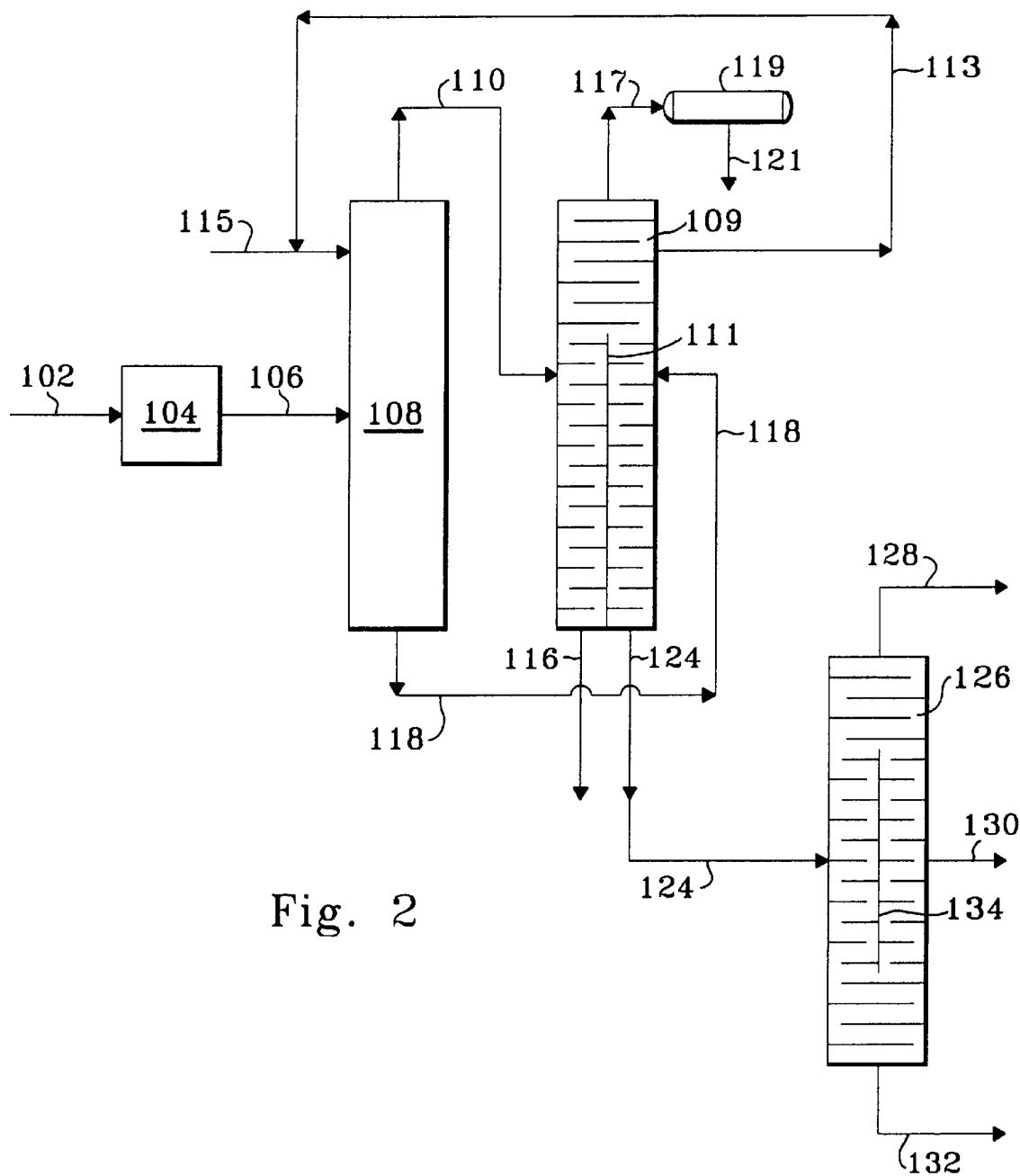
FIG. 2 is another highly simplified process flow diagram of a second embodiment of the invention showing the raffinate stream and the extract stream recovered from a simulated moving bed adsorptive separation zone being passed into an integrated fractionation zone to remove desorbent and form raffinate product and an extract product. The raffinate product is passed to the left-hand fractionation zone of a single dividing wall product recovery column to separate and recover the high-octane components.

In another embodiment of the invention, the extract column and the raffinate column described above are replaced by an integrated fractionation column. This specific embodiment is described with reference to FIG. 2. Reference to the specific arrangement for this invention for the specific embodiment of the invention is not meant to limit the scope to the details disclosed therein. Furthermore, FIG. 2 is a schematic illustration and does not show a number of details for the process arrangement such as pumps, compressors, valves, stabilizers and recycle lines which are well known to those skilled in the art. Feed is conducted via line 102 to isomerization zone 104, both of which are as described above. Isomerization zone effluent is conducted via line 106 to an adsorptive separation zone 108, which is as described above. Recycled (in line 113) and fresh desorbent (in line 115), a mixture of normal butane and isobutane, is conducted to adsorptive separation zone 108 via line 113. The preferred mode of operation of adsorptive separation zone 108 is a simulated moving bed, however, for ease of understanding, FIG. 2 shows a simplified simulated moving bed, i.e., the rotary valve and sub-beds are not shown. An extract stream containing normal alkanes and desorbent is removed from adsorptive separation zone 108 via line 110. A raffinate stream containing isomerized products and C7+ hydrocarbons is removed from adsorptive separation zone via line 118.

Integrated fractionation column 109 contains two parallel fractionation zones separated in the column by a substantially fluid tight vertical wall 111. The vertical wall is not necessarily centered in the column. Vertical wall 111 divides a large portion of column 109 into two parallel fractionation zones. The two zones are isolated from each other for the height of this wall and also at the bottom of the wall. This seal at the bottom of the first zone distinguishes the column from a true dividing wall column, hence the term integrated fractionation column. Thus there is no direct vapor or liquid flow between the two fractionation zones. The upper end of the fractionation zone receiving the raffinate stream is, however, open to the internal volume of column 109. Thus vapor and liquid can freely move between these two portions of the column. This opening of the top of each fractionation zone into a larger fractionation zone allows vapor from both parallel zones to flow upward. The two smaller zones are thus described as being in open communication with each other and this larger zone at this point in the column. Liquid flow downward may or may not be regulated between the zones. Both of the fractionation zones have independent reboiling means (not shown).

Extract stream 110 from adsorptive separation zone 108 will contain desorbent and normal paraffins, specifically normal pentane and normal hexane. Raffinate stream 118 from adsorptive separation zone 108 will contain isomerization products such as methylpentane, 2-methylpentane, 3-methylpentane, methylcyclopentane, cyclohexane, isopentane, 2,2,-dimethylbutane, 2,3-dimethylbutane, $C_7+$ and other trace compounds. Both extract stream 110 and raffinate stream 118 are directed to integrated fractionation column 109. The raffinate stream is introduced to the fractionation zone occupying portions of the right-hand side of the integrated fractionation column. This fractionation zone is separated from the other by substantially fluid tight vertical wall 111. The upper end of the fractionation zone receiving the raffinate stream is open to the internal volume of column 109. Thus, vapor or liquid can freely move between the two portions of the column. The more volatile desorbent components of raffinate stream 118 are fractionated upward out of the fractionation zones and emerge into the upper portion of column 109. The less volatile raffinate components, e.g., the branched paraffins are concentrated into a bottoms stream and removed from the first fractionation zone as the raffinate product in line 124.

Concurrently, extract stream 110 is delivered to a second vertical fractionation zone occupying a large portion of the left-hand side of column 109. The less volatile extract components, the normal pentane and normal hexane, are concentrated into a bottoms stream and removed from the first fractionation zone as the extract product via line 116. As with the first fractionation zone, the upper end of the second zone is in open communication with the upper section of column 109 which contains additional fractionation trays extending across the entire column cross section. Desorbents present in extract stream 110 are driven upward in the second fractionation zone and enter the top of fractionation column 109. The top of column 109 is a purification zone which is not intended for the separation of extract or raffinate compounds from the desorbent. This section may be used in the present embodiment to adjust the ratio of normal butane to isobutane to the desired ratio for the desorbent function. A stream of liquid phase desorbent in the desired ratio of normal butane to isobutane is removed from column 109 in line 113 and may be recycled to adsorptive separation zone 108. A vapor stream comprising desorbents 117 is removed from the top of column 109 and is passed through an overhead condenser 119 to form liquid desorbent which may be removed from condenser via line 121 and a portion of which may be recycled to the column for reflux.

Each of the first and second fractionation zones has independent reboiler systems (not shown). However, integrating the traditional distillation columns, one for the extract stream and one for the raffinate stream into a single integrated distillation column significantly reduces the necessary capital investment. Specifically, the overhead system for each of the traditional distillation columns is combined into a single overhead system on the integrated distillation column, thereby reducing capital and operational costs. The extract product in line 116 may be recycled to the isomerization zone for conversion of the normal alkanes to higher octane isomerized products. The raffinate product line 124 is introduced to the dividing wall fractionation column 126 having dividing wall 134 as described in the above embodiment to form a 2-methylpentane and 3-methylpentane stream in line 130 which is removed from an intermediate point of the second fractionation zone of the dividing wall fractionation column 126; a 2,2-dimethylbutane, 2,3-dimethylpentane, and isopentane stream in line 128 which is removed from a first end of the dividing wall fractionation column 126, and a methylcyclopentane, cyclohexane, and C7+ hydrocarbons stream in line 132 which is removed from a second end of the dividing wall fractionation column 126.

Figure 3:
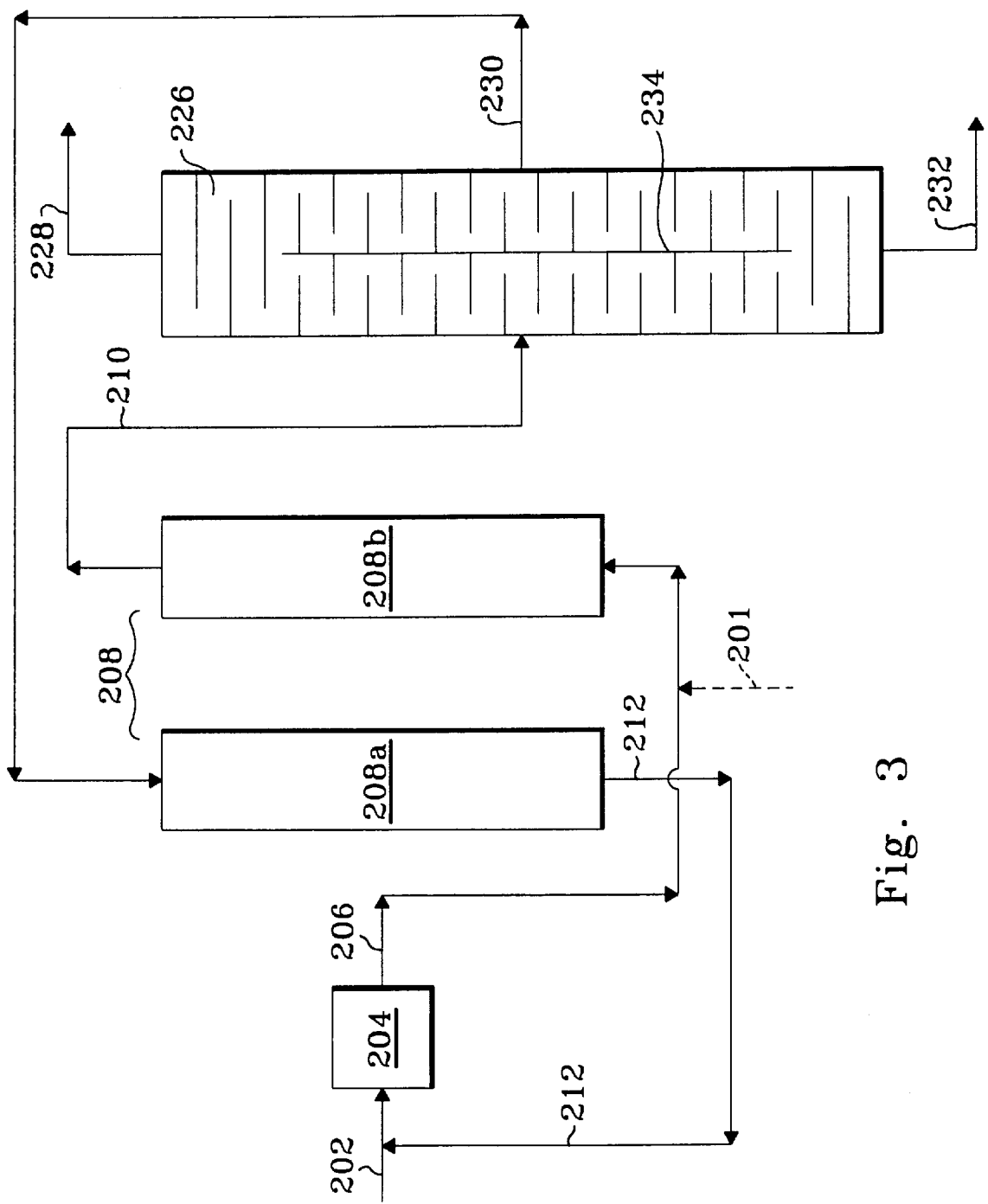
FIG. 3 is a highly simplified process flow diagram of another embodiment of the invention where the adsorptive separation zone is operated in a pressure swing adsorption mode. The less strongly adsorbed isomerized products are passed to the left-hand fractionation zone of a single dividing wall product recovery column to separate and recover the high-octane components. The separated low-octane components from the dividing wall product recovery column are used in the desorption of the normal alkanes from the pressure swing adsorption separation zone.

Yet another embodiment of the invention, one employing pressure swing adsorption, may by exemplified by FIG. 3. Reference to the specific arrangement for this invention for the specific embodiment of the invention is not meant to limit the scope to the details disclosed therein. Furthermore, FIG. 3 is a schematic illustration and does not show a number of details for the process arrangement such as pumps, compressors, valves, stabilizers and recycle lines which are well known to those skilled in the art. Feed is conducted via line 202 to isomerization zone 204, both of which are as described in detail above. Isomerization zone effluent is conducted via line 206 to an adsorptive separation zone 208, which is a pressure swing adsorption zone having bed 208a and 208b. Pressure swing adsorption is a known technique, and any known pressure swing operation may be used herein. FIG. 3 depicts the flow scheme at one point in time. It is readily understood by one skilled in the art that pressure swing operation would require that periodically a stream is redirected from the sub-bed actively performing a separation to a sub-bed that has been regenerated and vice versa. Similarly, the effluent of each sub-bed may be periodically redirected. FIG. 3 is depicting sub-bed 208b as the bed actively separating, and sub-bed 208a as the bed undergoing regeneration.

Isomerization zone effluent is conducted via line 206 to adsorptive separation zone sub-bed 208b where normal alkanes are adsorbed. An isomerized product stream containing isomerized products and C7+ hydrocarbons is removed from adsorptive separation zone sub-bed 208b via line 210. The isomerized product stream may contain a small amount of regenerant as well.

The isomerized product line 210 is introduced at the mid-section of the lefthand side, or first fractionation zone, of dividing wall fractionation column 226. The dimethylbutanes and isopentane along with a portion of the monomethyl pentanes are driven upward in the first fractionation zone and enter the top of column 226. A stream rich in dimethylbutanes and isopentane is removed from the top of the dividing wall column 226 in line 228. Line 228 may be passed through an overhead condenser (not shown) to form liquid delivered to the receiver. A liquid phase stream is removed from the receiver and divided into a first portion which is returned to the top of the dividing wall fractionation column as reflux and a second portion which is removed from the process (not shown).

Methylcyclopentane, cyclohexane, and $C_7+$ compounds and some monomethylpentanes drain down the first fractionation zone and enter the bottom of column 226. The monomethylpentanes are driven up into the second fractionation section. A stream rich in methylcyclopentane, cyclohexane, and $C_7+$ compounds is removed from the bottom of the dividing wall column 226 in line 232. A stream containing 2-methylpentane and 3-methylpentane is withdrawn from the dividing wall fractionation column in a side draw from the right-hand side, or second, fractionation zone in line 230.

The monomethylpentanes in line 230 are directed to the pressure swing adsorptive separation zone 208 for use as a regenerant. Line 230 is introduced to sub-bed 208a to desorb the normal alkanes. The effluent of sub-bed 208a contains normal alkanes and monomethylpentanes and is recycled in line 212 to reactor zone 204 for isomerization into components having a higher octane value. Alternatively, the feed stream may be introduced at a point between the isomerization zone and the adsorptive separation zone. For example, the feed stream may be introduced via line 201. The stream in line 228 may be combined with the stream in line 232 to form the overall isomerization process product.

What is claimed is:

1. An isomerization process having an adsorptive separation zone and a dividing wall fractionation zone, said process comprising:

contacting, in an isomerization zone, a feed stream containing at least normal pentane and normal hexane with an isomerization catalyst under isomerization conditions to convert at least a portion of the normal pentane and normal hexane into isomerized products and form an isomerization zone effluent containing normal pentane, normal hexane and isomerized products;

passing the isomerization zone effluent to an adsorptive separation zone comprising at least one bed of a selective adsorbent maintained at adsorption conditions under which the normal pentane and normal hexane are selectively retained on a quantity of the selective adsorbent, thus forming an isomerized product stream comprising at least the isomerized products;

desorbing the normal pentane and normal hexane under desorption conditions to yield a normal alkane stream comprising at least normal pentane and normal hexane;

passing the isomerized product stream into a dividing wall fractionation column operated at fractionation conditions and divided into at least a first and a second parallel fractionation zone by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and with the isomerized product stream entering the column at an intermediate point of the first fractionation zone;

removing a low-octane stream comprising 2-methylpentane and 3-methylpentane from an intermediate point of the second fractionation zone of the dividing wall fractionation column;

removing a first high-octane stream from a first end of the dividing wall fractionation column, and removing a second high-octane stream from a second end of the dividing wall fractionation column.

2. The process of claim 1 wherein the adsorptive separation zone is operated in mode selected from the group consisting of a simulated moving bed mode and a pressure swing adsorption mode.

3. The process of claim 1 further comprising collecting upward flow of vapor from the lower section of the dividing wall fractionation column into the first and second fractionation zones and then dividing between the first and second fractionation zones in a controlled manner.

4. The process of claim 1 wherein the desorbing employs a desorbent and the isomerized product stream and the normal alkane stream further comprise the desorbent.

5. The process of claim 4 further comprising passing the normal alkane stream to a fractionation column to separate the desorbent from the normal alkane stream and recycling the resulting desorbent-reduced normal alkane stream to the isomerization zone.

6. The process of claim 5 further comprising recycling the separated desorbent to the adsorptive separation zone.

7. The process of claim 4 further comprising passing the isomerized product stream to a fractionation column to separate the desorbent from the isomerized product stream prior to entering the dividing wall fractionation column.

8. The process of claim 7 further comprising recycling the separated desorbent to the adsorptive separation zone.

9. An isomerization process having an adsorptive separation zone, an integrated fractionation zone, and a dividing wall fractionation zone, said process comprising:

contacting, in an isomerization zone, a feed stream containing at least normal pentane and normal hexane with an isomerization catalyst under isomerization conditions to convert at least a portion of the normal pentane and normal hexane into isomerized products and form an isomerization zone effluent containing normal pentane, normal hexane and isomerized products;

passing the isomerization zone effluent to an adsorptive separation zone comprising a bed of a selective adsorbent maintained at adsorption conditions under which the normal pentane and normal hexane are selectively retained on a quantity of the selective adsorbent, thus forming a raffinate stream comprising the isomerized products and desorbent formerly present in the quantity of the selective adsorbent;

passing desorbent into contact with said quantity of the selective adsorbent which has retained the normal pentane and normal hexane under desorption conditions to yield an extract stream comprising normal pentane, normal hexane, and the desorbent;

passing the extract stream into an integrated fractionation column operated at fractionation conditions and divided into at least a first and a second vertical fractionation zone, with each zone having an upper and a lower end located within the fractionation column, with the first and second fractionation zones being in open communication at their upper ends at a first end of the column and with the extract stream entering the fractionation column at an intermediate point of the first fractionation zone passing the raffinate stream into an intermediate point of the second fractionation zone of the integrated fractionation column;

removing an extract product stream from the lower end of the first fractionation zone, said lower end of the first fractionation zone not being in communication with the second fractionation zone and being located at the second end of the integrated fractionation column;

removing a raffinate product stream from the lower end of the second fractionation zone, said lower end of the second fractionation zone not being in communication with the first fractionation zone and being located at the second end of the Integrated fractionation column;

removing a desorbent stream comprising the desorbent from the first end of the integrated fractionation column;

passing the raffinate product stream into a dividing wall fractionation column operated at fractionation conditions and divided into at least two parallel fractionation zones, zone A and zone B, by a dividing wall, with zone A and zone B each having an upper and a lower end located within the fractionation column, with zone A and zone B being in open communication at their upper ends with an undivided upper section of the fractionation column and in open communication at their lower ends with an undivided lower section of the fractionation column, and with the raffinate product stream entering the column at an intermediate point of the zone A;

removing a low-octane stream comprising 2-methylpentane and 3-methylpentane from an intermediate point of zone B of the dividing wall fractionation column;

removing a first high-octane stream from a first end of the dividing wall fractionation column, and removing a second high-octane stream from a second end of the dividing wall fractionation column.

10. The process of claim 9 wherein the adsorptive separation zone is operated in a simulated moving bed mode or a pressure swing adsorption mode.

11. The process of claim 9 further comprising recycling the extract product stream to the isomerization zone.

12. The process of claim 9 further comprising recycling the separated desorbent from the integrated fractionation column to the adsorptive separation zone.

13. The process of claim 9 further comprising collecting upward flow of vapor from the lower section of the dividing wall fractionation column into the first and second fractionation zones and then dividing between the first and second fractionation zones in a controlled manner.

14. The process of claim 11 wherein the feed stream to the isomerization zone is the recycled extract product stream, and further comprising introducing a fresh feed stream containing normal pentane and normal hexane to the adsorptive separation zone.

15. An isomerization process having an adsorptive separation zone and a dividing wall fractionation zone, said process comprising:

contacting, in an isomerization zone, a normal alkane stream containing at least normal pentane and normal hexane from an adsorptive separation zone with an isomerization catalyst under isomerization conditions to convert at least a portion of the normal pentane and normal hexane into isomerized products and form an isomerization zone effluent containing normal pentane, normal hexane and isomerized products;

passing a feed stream containing at least normal pentane and normal hexane and the isomerization zone effluent to an adsorptive separation zone comprising at least one bed of a selective adsorbent maintained at adsorption conditions under which the normal pentane and normal hexane are selectively retained on a quantity of the selective adsorbent, thus forming an isomerized product stream comprising at least the isomerized products;

desorbing the normal pentane and normal hexane under desorption conditions to yield the normal alkane stream comprising at least normal pentane and normal hexane;

passing the isomerized product stream into a dividing wall fractionation column operated at fractionation conditions and divided into at least a first and a second parallel fractionation zones by a dividing wall, with the first and the second fractionation zones each having an upper and a lower end located within the fractionation column, with the first and second fractionation zones being in open communication at their upper ends with an undivided upper section of the fractionation column and in open communication at their lower ends with an undivided lower section of the fractionation column, and With the isomerized product stream entering the column at an intermediate point of the first fractionation zone;

removing a low-octane stream comprising 2-methylpentane and 3-methylpentane from an intermediate point of the second fractionation zone of the dividing wall fractionation column;

removing a first high-octane stream from a first end of the dividing wall fractionation column, and removing a second high-octane stream from a second end of the dividing wall fractionation column.

16. The process of claim 15 wherein the adsorptive separation zone is operated in a mode selected from the group consisting of a simulated moving bed mode and a pressure swing adsorption mode.

* * * * *